United States Patent [19]
Buffaloe, IV et al.

[11] Patent Number: 5,510,716
[45] Date of Patent: Apr. 23, 1996

[54] DIFFERENTIAL CONDUCTIVITY RECIRCULATION MONITOR

[75] Inventors: George W. Buffaloe, IV, Arvada; Francis T. Ogawa, Lakewood; James M. Brugger, Boulder, all of Colo.

[73] Assignee: COBE Laboratories, Inc., Lakewood, Colo.

[21] Appl. No.: 332,647

[22] Filed: Nov. 1, 1994

Related U.S. Application Data

[63] Continuation of Ser. No. 954,584, Sep. 30, 1992, abandoned.

[51] Int. Cl.⁶ ............................................. B01D 61/32
[52] U.S. Cl. ............................. 324/445; 210/646; 604/4; 604/65
[58] Field of Search ..................... 324/439, 445, 324/450, 722; 210/96.1, 646; 436/150; 604/30, 4, 65, 246; 73/861.07, 861.11, 861.08, 861.16

[56] References Cited

U.S. PATENT DOCUMENTS

| | | | |
|---|---|---|---|
| 2,709,785 | 5/1955 | Fielden | 324/445 X |
| 3,396,331 | 8/1968 | Sperry, III | 324/445 |
| 3,404,336 | 10/1968 | Rosenthal | 324/445 |
| 3,482,575 | 12/1969 | Claff | 604/4 |
| 3,491,592 | 1/1970 | Evers et al. | 73/861.07 |
| 3,619,423 | 11/1971 | Galetti | 210/646 |
| 3,867,688 | 2/1975 | Koski | 324/445 |
| 3,980,946 | 9/1976 | Fleury | 324/445 |
| 4,081,372 | 3/1978 | Atkin et al. | 210/94 |
| 4,136,563 | 1/1979 | Mueller et al. | 73/861.03 |
| 4,138,639 | 2/1979 | Hutchins | 324/445 X |
| 4,181,610 | 1/1980 | Shintani et al. | 210/96.2 |
| 4,361,049 | 11/1982 | Volgyesi | 73/861.07 |
| 4,508,622 | 4/1985 | Polaschegg et al. | |
| 4,650,458 | 3/1987 | Dahlberg et al. | 604/30 |
| 4,739,492 | 4/1988 | Cochran | 324/445 X |

(List continued on next page.)

FOREIGN PATENT DOCUMENTS

| | | |
|---|---|---|
| 0097366 | 1/1984 | European Pat. Off. . |
| 0272414 | 6/1988 | European Pat. Off. . |
| 0272414A2 | 6/1988 | European Pat. Off. . |
| 36990 | 10/1977 | Japan . |
| 190873 | 9/1985 | Japan . |
| 2026508 | 5/1992 | Spain . |
| 521891 | 10/1976 | U.S.S.R. . |
| 1013853 | 4/1983 | U.S.S.R. . |
| 2093192 | 8/1982 | United Kingdom . |

OTHER PUBLICATIONS

C. Aldridge et al., "The Assessment of Arterivenous Fistulae Created for Haemodialysis from Pressure and Thermal Dilution Measurements, Journal of Medical Engineering & Technology," vol. 8, No. 3, pp. 118–124, May/Jun. 1984, U.K.

C. Aldridge et al., "Instrument Design for the Bedside Assessment of Arteriovenous Fistulae in Haemodialysis Patients," Proceedings EDTNA–ERCA, vol. 14, pp. 255–260, 1985, U.K. (month unavailable).

(List continued on next page.)

*Primary Examiner*—Kenneth A. Wieder
*Assistant Examiner*—Christopher M. Tobin
*Attorney, Agent, or Firm*—Bruce R. Winsor

[57] ABSTRACT

A differential conductivity recirculation monitor quantitatively determines the degree of recirculation in a fistula by comparing the conductivity of blood entering the fistula to the conductivity of blood being withdrawn from the fistula. A discrete quantity of a high conductivity marker fluid is injected into the blood entering the fistula, altering the conductivity of the blood entering the fistula. The altered conductivity blood enters the fistula and, if recirculation is present, co-mingles with blood in the fistula, altering the conductivity of the blood ion the fistula in proportion to the degree of recirculation. Blood withdrawn from the fistula has an altered conductivity related to the degree of recirculation. Quantitative values of the conductivity of the altered conductivity blood entering the fistula and the conductivity of the blood being withdrawn from the fistula are measured and a difference determined. The determined difference between the conductivities is used to determine a quantitative measurement of the degree of recirculation in the fistula.

44 Claims, 6 Drawing Sheets

U.S. PATENT DOCUMENTS

| | | | |
|---|---|---|---|
| 4,740,755 | 4/1988 | Ogawa | 324/445 |
| 4,825,168 | 4/1989 | Ogawa et al. | |
| 4,995,268 | 2/1991 | Ash et al. | 604/65 X |
| 5,004,459 | 4/1991 | Peabody et al. | 604/29 |
| 5,092,836 | 3/1992 | Polaschegg | 210/646 |
| 5,312,550 | 5/1994 | Hester | 210/646 |

OTHER PUBLICATIONS

C. Aldridge, "The Use and Management of Arteriovenous Fistulae Fact and Fiction", EDTNA ERCA, Journal SVII-4, pp. 29–35, Oct. 1991, United Kingdom Examiner.

Joseph J. Carr, "Integration of Decaying Exponential Sensor Output Signals", Sensors, pp. 28–34, Jul. 1989, Virginia.

J. Daugirdas, "The Fourth Annual Advanced Dialysis Technical Symposium", Dialysis & Transplantation, vol. 17, No. 8, pp. 432–433, Aug. 1988, Illinois.

Fresenius, "BTM 4008", Nov. 1993, Germany and translation from German to English.

Gambro, "Fistula Assessment Monitor FAM 10," approximately 1985, U.K. (month unavailable).

Gambro, "Fistula Assessment Monitor FAM 10 Operator's Manual," approximately 1985, U.K. (month unavailable).

Gambro, "Fistula Assessment Monitor FAM 10 Service Manual," approximately 1985, Sidcup, Kent, U.K. (Month unavailable).

J. S. Gani et al., "Use of the Fistula Assessment Monitor to Detect Stenoses in Access Fistulae," (abstract) Australian Society of Nephrology, 1989, Australia (month unavailable).

Jonathan S. Gani, Use of the Fistula Assessment Monitor to Detect Stenoses in Access Fistulae, American Journal of Kidney Diseases, vol. XVII, No. 3, pp. 303–306, Mar. 1991, Newcastle, Australia.

R. N. Greenwood et al. "Assessment of Arteriovenous Fistulae from Pressure and Recirculation Studies. Clinical Experience in 186 Fistulae,", Abstract, p. 106, 1985, London, U.K. month unavailable.

R. N. Greenwood et al., Assessment of Arteriovenous Fistulas From Pressure and Recirculation Studies: Clinical Experience in 215 Upper Limb Fistulas, EDTA–ERA, vol. 22, pp. 296–302, 1985, London, U.K. month unavailable.

R. N. Greenwood et al., "Assessment of Arteriovenous Fistulae from Pressure and Thermal Dilution Studies: Clinical Experience in Forearm Fistulae," Clinical Nephrology, vol. 23, No. 4, pp. 189–197, 1985, U.K. month unavailable.

L. Goldstein et al., "The Assessment of Arteriovenous Fistulae From Pressure and Recirculation Studies", Porc EDTNA–ERCA, vol. 14, pp. 207–215, 1985, United Kingdom month unavailable.

Lynn W. Hart et al., "A Noninvasive Electromagnetic Conductivity Sensor for Biomedical Applications", IEEE Transactions on Biomedical Engineering, vol. 35, No. 12, pp. 1011–1022, Dec. 1988, Maryland.

Robert L. Hester et al., "The Determination of Hemodialysis Blood Recirculation Using Blood Urea Nitrogen Measurements," American Journal of Kidney Diseases, vol. XX, No. 6, pp. 598–602, Dec. 1992, Mississippi.

R. L. Hester et al., "Non–invasive Measurement of Recirculation in the Dialysis Patient", Abstract No. 7, Jul. 1992.

Robert L. Hester et al., "Non–invasive Determination of Recirculation in the Patient on Dialysis," ASAIO Journal, pp. M190–M193, 1992, Mississippi (month unavailable).

M. Kramer et al., "Automated Measurement of Recirculation," EDTNA–ERCA, Journal, vol. XIX, No. 2, Apr. 1993.

Matthias Kramer et al., "A Device for Control of Thermal Parameters and Recirculation Measurement in Hemodialysis," Nov., 1992, Germany.

John L. Nosher, "Death Taxes, and Vascular Access Dysfunction", Seminars in Dialysis, vol. 4, No. 2, pp. 67–68, Apr.–Jun. 1991, New Jersey.

Richard A. Sherman, "Recirculation Revisited", Seminars in Dialysis, vol. 4, No. 4, pp. 221–223, Oct.–Dec. 1991, New Jersey.

McKamy Smith, "Cardiac Output Determined by the Saline Conductivity Method Using an Extraarterial Conductivity Cell", Cardiovascular Research Center Bulletin, vol. 5, No. 4, pp. 123–134, Apr.–Jun. 1967, Texas.

Mogens Thomsen et al., "Evaluation of Clinical Examination Preceding Surgical Treatment of AV–Fistula Problems," Acta Chir Scand, vol. 151, pp. 133–137, 1985, Sweden (month unavailable).

Transonic Systems, Inc., Access Flow & Recirculation Measured During Hemodialysis, Oct. 1994, New York.

Transonic Systems Inc, "Transonic Hemodialysis Monitor Measures Access Flow Recirculation Cardiac Output Routinely during Dialyis", Apr. 1995.

Nikolai M. Krivitski, "Novel Method to Measure Access Flow During Hemodialysis by Ultrasound Velocity Dilution Technique", Jul. 27, 1985, ASAIO Journal, pp. 0014–0018.

Thomas A. Depner and Nikolai M. Krivitski, "Clinical Measurement of Blood Flow in Hemodialysis Access Fistulae and Grafts by Ultrasound Dilution", Jul. 27, 1985, ASAIO Journal, pp. 0018–0022.

Thomas A. Depner et al., "Hemodialysis Access Recirculation Measured by Ultrasound Dilution", Jul. 27, 1995, ASAIO Journal, pp. 0022–0026.

N. M. Krivitski, "Novel Method to Measure Access Flow During Hemodialysis by Ultrasound Dilution (UD)", ASAIO Journal 1995.

Nikolai M. Krivitski, "Theory and Validation of Access Flow Measurement by Dilution Technique during Hemodialysis", Kidney International, vol. 48 (1995), pp. 244–250.

N. M. Krvitski, "Accuracy of Ultrasound Dilution Method to Measure Access Flow (AF) in Hemodialysis", XIIIth International Congress of Nephrology, Abstract, 1995.

Nikolai Krivitski, Ph.D. "New Method to Measure Recirculation (Rc) and Access Flow During Hemodialysis (HD)", American Nephrology Nurses' Association 26th National Symposium Exhibitor Continuing Education Program, Abstract, 1995.

T. Depner, "Changes in Access Blood Flow (Qac) and Appearance of Recirculation (RC) During Hemodialysis", XIIIth International Congress of Nephrology, Abstract, 1995.

T. A. Depner et al., "Hemodialysis Access Recirculation (Rc) Measured by Ultrasound Dilution", ASAIO Journal 1995 Abstracts, Supplement to Jan.–Mar. 1995 vol. 41, No. 1, p. 80.

T. A. Depner and N. M. Krivitski, "Clinical Measurement of Blood Flow in Hemodialysis Access Fistulae and Grafts by Ultrasound Dilution", ASAIO Journal 1995 Abstracts, Supplement to Jan.–Mar. 1995 vol. 41, No. 1, p. 80.

N. M. Krivitski, "Cardia Output Measurement in Extracorporeal Systems by Ultrasound Velocity Dilution", ASAIO Abstracts, 1994, p. 82.

Jeffrey Sands, et al., "The Effect of Doppler Flow Screening Studies and Elective Revisions on Dialysis Access Failure", Reprint from ASAIO Transactions, Jul.–Sep., 1992, pp. M524–M527.

Salamon et al. "Translation: low frequency electrodeless conductometer for measuring the electrical conductivity of solutions", 1959, Industrial Group Headquarters, Risley, Risley, Warrington, Lancashire, GB.

Robert L. Hester, Ph.D., "A New Technique for Determining Recirculation in the ESRD Patient", *Nephrology News & Issues*, pp. 44–45, Jun. 1993, Jackson, MS.

5,510,716

DIFFERENTIAL CONDUCTIVITY RECIRCULATION MONITOR

This application si continuation of application Ser. No. 07/954,584, filed Sep. 30, 1992, now abandoned.

FIELD OF THE INVENTION

This invention relates to measurement of recirculation efficiency. More particularly, this invention relates to measurement of the recirculation efficiency of a biological or medical fluid during a medical procedure or for diagnostic purposes.

BACKGROUND OF THE INVENTION

In many medical situations it is desirable to quantitatively determine, or measure, the recirculation rate or the recirculation efficiency of a biological or medical fluid to increase the benefits of, or decrease the time required for, a therapeutic treatment, or for diagnostic purposes. For example, hemodialysis (herein "dialysis") is an inconvenient, expensive, and uncomfortable medical procedure. It is, therefore, widely recognized as desirable to minimize the amount of time required to complete the procedure and to achieve a desired level of treatment.

In dialysis, a joint is typically surgically created between a vein and an artery of a patient undergoing dialysis. The joint provides a blood access site where an inlet line to a dialysis apparatus and an outlet line from the dialysis apparatus are connected. The inlet line draws blood to be treated from the patient, while the outlet line returns treated blood to the patient.

This joint may be an arteriovenous fistula, which is a direct connection of one of the patient's veins to one of the patient's arteries. Alternatively the joint may be a synthetic or animal organ graft connecting the vein to the artery. As used herein, the term "fistula" refers to any surgically created or implanted joint between one of the patient's veins and one of the patient's arteries, however created.

In the fistula a portion of the treated blood returned to the patient by the outlet line may recirculate. Recirculating treated blood will co-mingle with untreated blood being withdrawn from the patient by the inlet line. This recirculation, and the resulting co-mingling of treated and untreated blood, is dependent, in part, on the rate at which blood is withdrawn from and returned to the patient. The relationship is typically a direct, but non-linear relationship. It can be readily appreciated that the dialysis apparatus will operate most effectively, and the desired level of treatment achieved in the shortest period of time, when the inlet line is drawing only untreated blood at the maximum flow rate capability of the dialysis apparatus consistent with patient safety. As a practical matter, however, as flow rate through the dialysis apparatus is increased, the proportion of recirculated treated blood in the blood being drawn through the inlet line is increased. In order to select the flow rate through the dialysis apparatus, it is desirable to know the proportion of recirculated treated blood in the blood being withdrawn from the patient by the inlet line. This proportion is referred to herein as the "recirculation ratio". The recirculation ratio can also be defined as the ratio between the flow of recirculated blood being withdrawn from the fistula to the flow of blood being returned to the fistula. Recirculation efficiency may then be defined by the relationship:

$$E = 1 - R$$

where

E=Recirculation efficiency

R=Recirculation ratio

Alternatively, recirculation efficiency may be equivalently expressed as the ratio of blood flow being returned to the fistula, but not being recirculated, to the total blood flow being returned to the fistula. Knowing the recirculation efficiency, the dialysis apparatus operator can adjust the flow rate through the dialysis apparatus to minimize the time required to achieve the desired level of treatment.

In the prior art, quantitative determination of recirculation ratio or recirculation efficiency has typically required laboratory testing, such as blood urea nitrogen tests, which take considerable amounts of time and which require withdrawing blood from the patient, which is recognized as undesirable.

A method and apparatus for qualitatively detecting the presence or absence of recirculation in a fistula is described in "FAM 10 Fistula Flow Studies and their Interpretation" published by Gambro, Ltd. based on research performed in 1982. The Gambro method and apparatus injects a quantity of a fluid having an optical density less than the optical density of treated blood into the dialysis apparatus outlet line. A resulting change in the optical density of the blood being drawn through the dialysis apparatus inlet line is qualitatively detected as indicative of the presence of recirculation. The Gambro method and apparatus does not quantitatively determine or measure a recirculation ratio or recirculation efficiency.

Devices which qualitatively determine recirculation by thermal techniques are also known.

A quantitative measurement of the recirculation efficiency of a bodily or medical fluid is useful in other therapeutic and diagnostic procedures as well. For example, recirculation ratios and efficiencies are useful for determining cardiac output, intervascular recirculation, recirculation in non-surgically created access sites, and dialyzer performance from either the blood side or the dialysate side of the dialyzer, or both.

It is known that the electrical conductivity of a fluid in a closed non-metallic conduit can be measured without contact with the fluid by inducing an alternating electrical current in a conduit loop comprising a closed electrical path of known cross sectional area and length. The magnitude of the current thus induced is proportional to the conductivity of the fluid. The induced current magnitude may then be detected by inductive sensing to give a quantitative indication of fluid conductivity. A conductivity cell for measuring the conductivity of a fluid in a closed conduit without contact with the fluid is described in U.S. Pat. No. 4,740,755 entitled "Remote Conductivity Sensor Having Transformer Coupling In A Fluid Flow Path," issued Apr. 26, 1988 to Ogawa and assigned to the assignee of the present invention, the disclosure of which is hereby incorporated herein by reference.

It is against this background that the differential conductivity recirculation monitor of the present invention developed.

SUMMARY OF THE INVENTION

A significant aspect of the present invention is a method and apparatus for quantitatively measuring the recirculation efficiency of a fluid in a vessel, such as a fistula, containing the fluid and from which fluid is being withdrawn through a first, or inlet, line and to which the fluid is being returned through a second, or outlet, line. In accordance with this aspect of the invention a discrete quantity (referred to herein as a "bolus") of a marker fluid having an electrical conductivity different from the electrical conductivity of the fluid flowing in the outlet line is injected into the fluid flowing in the outlet line. The marker fluid alters the conductivity of the fluid in the outlet line. The altered conductivity fluid in the outlet line enters the vessel and, if recirculation is present, co-mingles with the fluid in the vessel. The conductivity of the fluid in the vessel is thus altered in proportion to the degree of recirculation. The inlet line withdraws from the vessel fluid having an altered conductivity related to the degree of recirculation. Quantitative values of the conductivity of the altered conductivity fluid in the outlet line and the conductivity of the fluid in the inlet line are measured and a difference determined. The determined difference between the conductivity is used to determine a quantitative measurement of the recirculation efficiency in the vessel.

Another significant aspect of the present invention is a method and apparatus for quantitatively determining a difference in the conductivity of a first and a second fluid. In accordance with this aspect of the invention the first fluid is placed in a first conductivity cell and the second fluid is placed in a second conductivity cell. Each conductivity cell is a conduit of predetermined cross sectional area formed into a ring-like configuration of predetermined circumference. The configuration of each conductivity cell confines the fluid therein into an electrical path having a predetermined cross sectional area and a predetermined path length. An excitation coil excited by an alternating electrical current is proximate to the conduits of both conductivity cells at an excitation location. A first fluid alternating current is induced in the first fluid in relation to the conductivity of the first fluid. A second fluid alternating current is induced in the second fluid in relation to the conductivity of the second fluid. The first and second fluid alternating currents flow in the first and second fluids in substantially the same electrical direction at the excitation location. A sensing coil is proximate to the conduits of the first and second conductivity cells at a sensing location. The tubes of the first and second conductivity cells are oriented at the sensing location so that the first fluid alternating current flows in a substantially opposite electrical direction from the direction of the second fluid alternating current. A sensed alternating current is induced in the sensing coil by the first fluid alternating current and the second fluid alternating current that is proportional to the difference between the first and second fluid alternating currents. The sensed alternating current is quantitatively indicative of the difference between the conductivities of the first and second fluids.

Still another significant aspect of the present invention is a tubing set adapted for use with an apparatus incorporating the present invention. In accordance with this aspect of the invention a disposable tubing set, such as are typically used in dialysis apparatuses and other medical apparatuses, has a conductivity cell formed into each of two tubes of the tubing set. Each conductivity cell is a conduit of predetermined cross sectional area formed into a ring-like of predetermined circumference. Each conductivity cell has formed to it an upstream tube in fluid communication with the conductivity cell and a downstream tube in fluid communication with the conductivity cell, the upstream and downstream tubes being oriented so that the ring-like configuration of the conductivity cell forms two tubing branches fluidly interconnecting the upstream tube to the downstream tube.

A further significant aspect of the present invention is a medical apparatus incorporating the recirculation monitor.

A more complete appreciation of the present invention and its scope can be obtained from understanding the accompanying drawings, which are briefly summarized below, the following detailed description of a presently preferred embodiment of the invention, and the appended claims.

DETAILED DESCRIPTION OF THE PREFERRED EMBODIMENT

Figure 1:
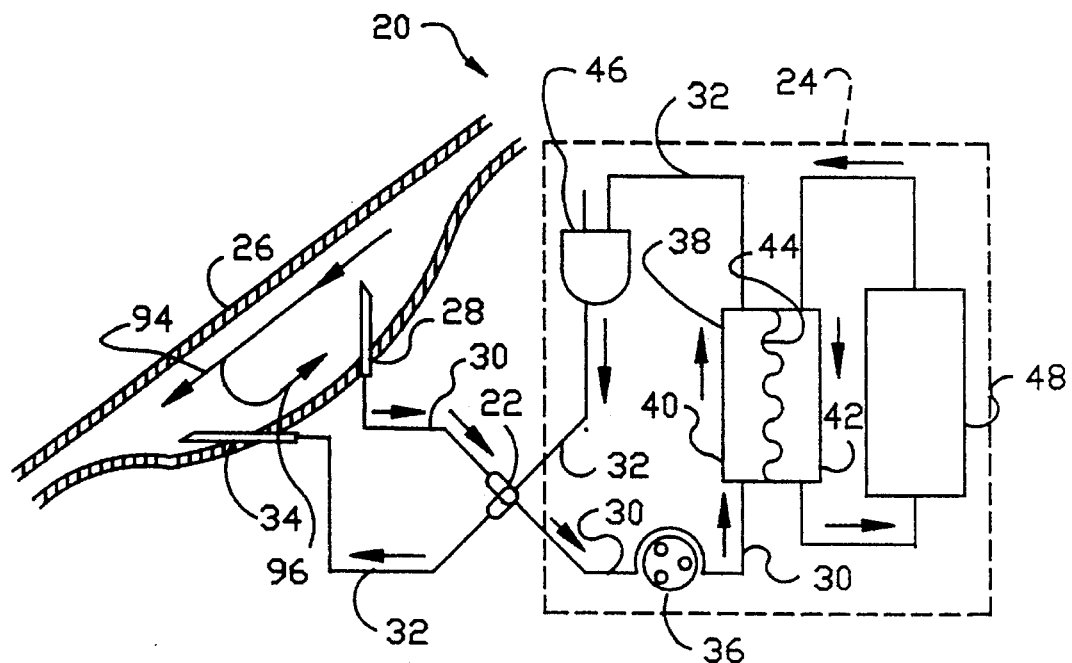
FIG. 1 is a schematic diagram of a dialysis system incorporating a differential conductivity recirculation monitor in accordance with the present invention.

FIG. 1 illustrates a dialysis system 20 incorporating a differential conductivity recirculation monitor 22 for determining and displaying recirculation efficiency in accordance with the present invention. The dialysis system 20, which is one example of a medical system with which the present invention may be advantageously used, comprises a dialysis apparatus 24 connected to a fistula 26 surgically formed in a dialysis patient (not shown). Untreated blood is drawn from the fistula 26 through a dialyzer inlet needle 28 and a dialyzer inlet line 30. Treated blood is returned to the fistula through a dialyzer outlet line 32 and a dialyzer outlet needle 34. The recirculation monitor 22 is located in the dialyzer inlet and outlet lines 30 and 32 at a point intermediate between the fistula 26 and the dialysis apparatus 24.

The dialysis apparatus 24 comprises a blood pump 36 typically a peristaltic pump, a dialyzer 38 having a blood compartment 40 and a dialysate compartment 42 separated by a semi-permeable membrane 44, a bubble trap 46 and a dialysate generator 48. Blood is drawn from the fistula 26 by the action of the blood pump 36 and passed through the blood compartment 40 of the dialyzer 38. The membrane 44 allows transfer of impurities in the blood, such as urea and creatinine, from the blood compartment 40 to the dialysate compartment 42 of the dialyzer 38. The dialysate compartment 42 is connected to a dialysate generator 48 which generates the dialysate, a liquid isotonic to blood, and circulates it through the dialysate compartment 44.

Figure 2:
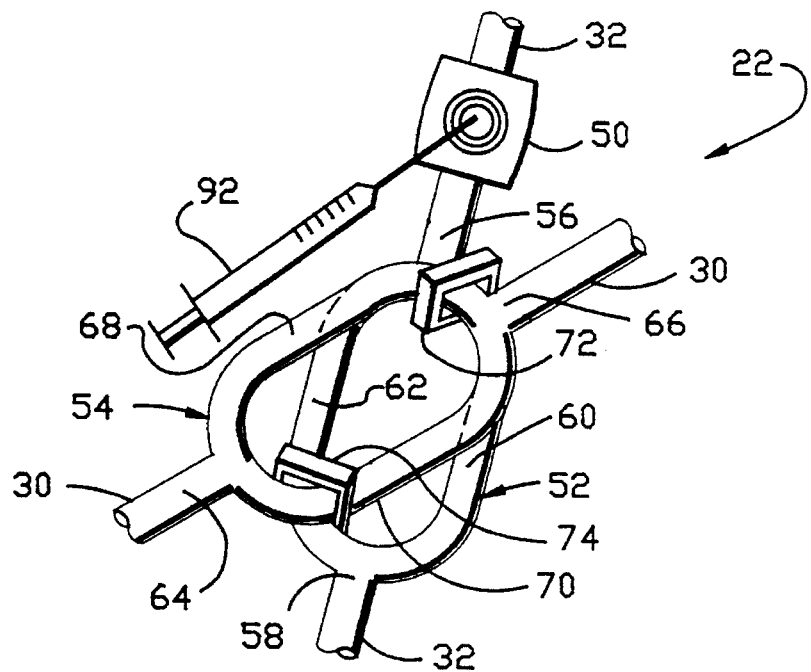
FIG. 2 is a partial perspective view illustrating the functional elements of the differential conductivity recirculation monitor shown in FIG. 1.
Figure 3:
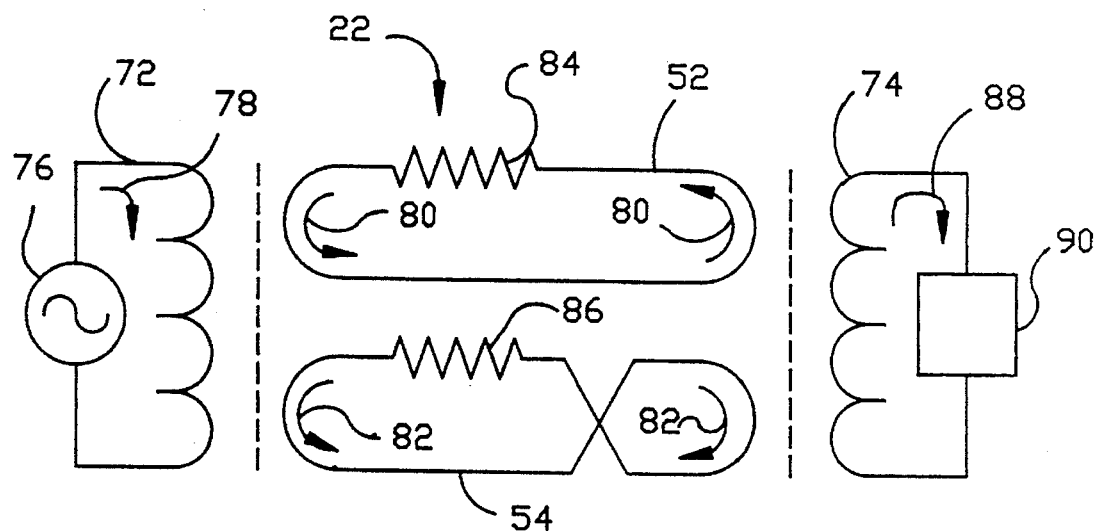
FIG. 3 is an electrical schematic diagram of the differential conductivity recirculation monitor shown in FIG. 2.

The principles of operation of the differential conductivity recirculation detector 22 of the present invention are explained in conjunction with FIGS. 2 and 3. The recirculation detector 22 comprises a needle access site 50 in the dialyzer outlet line 32. A first or outlet conductivity cell 52 is located in the dialyzer outlet line 32 downstream of the needle access site 50. A second or inlet conductivity cell 54 is located in the dialyzer inlet line 28. The first conductivity cell 52 comprises an upstream connection 56, a downstream connection 58 and first and second tubing branches 60 and 62, respectively, each of which interconnect the upstream connection 56 with the downstream connection 58. Treated blood from the dialyzer flows in the dialyzer outlet line 32 through the needle access site 50 to the upstream connection 56. At the upstream connection 56 the flow splits approximately equally with a portion of the treated blood flowing in each of the two tubing branches 60 and 62 of the outlet conductivity cell 52. The flow rejoins at the downstream connection 58 and flows through the dialyzer outlet line 32 to the fistula 26 (FIG. 1). Similarly, the inlet conductivity cell 54 comprises an upstream connection 64, a downstream connection 66 and third and fourth tubing branches 68 and 70, respectively, which each connect the upstream connection 64 to the downstream connection 66. Untreated blood from the fistula 26 flowing in the dialyzer inlet line 30, enters the inlet conductivity cell 54 at the upstream connection 64 divides approximately equally between the third and fourth tubing branches 68 and 70 and rejoins at the downstream connection 66 to the inlet conductivity cell 54. Each one of the tubing branches 60, 62, 68 and 70 has the same cross sectional area and length as each other one of the tubing branches.

The blood, or other biological or medical fluid, flowing in each conductivity cell 52 and 54 comprises an electrical circuit. The electrical circuit is a path for circulation of an electrical current from the upstream connection, through one of the tubing branches, to the downstream connection and from the downstream connection through the other one of the tubing branches to the upstream connection.

The outlet conductivity cell 52 and the inlet conductivity cell 54 are positioned adjacent to each other in an angular relationship resembling a pretzel so that the first tubing branch 60 of the outlet conductivity cell 52 is positioned parallel to the third tubing branch 68 of the inlet conductivity cell at an excitation location. The conductivity cells are further positioned so that the second tubing branch 62 of the outlet conductivity cell 52 crosses the fourth tubing branch 70 of the inlet conductivity cell 54 at an angle, approximately sixty degrees in the preferred embodiment, at a sensing location. An excitation coil 72 encircles the first tubing branch 60 of the outlet conductivity cell 52 and the third tubing branch 68 of the inlet conductivity cell 54 at the excitation location. A sensing coil 74 encircles the second tubing branch 62 of the outlet conductivity cell 52 and the fourth tubing branch 70 of the inlet conductivity cell 54 at the sensing location.

An electrical circuit, as is illustrated schematically in FIG. 3, is thus formed. The excitation coil 72 is inductively coupled to the outlet conductivity cell 52 and the inlet conductivity cell 54. When a source of excitation energy 76 causes an alternating excitation current, illustrated by direction arrow 78, to flow in the excitation coil 72 a changing magnetic field is generated which causes an electrical current, illustrated by the direction arrow 80, to flow in the blood in the outlet conductivity cell 52 and causes another electrical current, illustrated by direction arrow 82, to flow in the same electrical direction in the blood in the inlet conductivity cell 54. Since the conductivity cells 52 and 54 are formed to create electrical paths of equal cross sectional area and equal path length the electrical conductance of the paths, as illustrated by the schematic resistors 84 and 86, and thus the magnitude of the induced currents 80 and 82, will be related to the conductivity of the blood in the respective conductivity cells 52 and 54.

The induced currents 80 and 82 flowing in the outlet and inlet conductivity cells 52 and 54 generate a changing magnetic field at the sensing location that induces a sensed current, illustrated by direction arrow 88, in the sensing coil 74. The induced currents 80 and 82 are in opposite electrical directions so that the magnetic field at the sensing location has a magnitude proportional to the difference between the induced currents. The sensed current 88 is proportional to the magnetic field at the sensing location where the sensing coil 74 encircles the second and fourth tubing branches 62 and 70, respectively. The sensed current 88 induced in the sensing transformer 74 is therefore proportional to a difference between the induced currents 80 and 82 in the outlet and inlet conductivity cells 52 and 54, respectively. The induced currents 80 and 82 in the outlet and inlet conductivity cells 52 and 54, respectively, are related to the conductivity of the fluids in those chambers. Therefore, the magnitude of the sensed current 88 induced in the sensing coil 74 will be related to the difference between the conductivities of the fluids in the outlet and inlet conductivity cells 52 and 54. The sensed current 88 is delivered to, and interpreted by a sensing logic and display circuit 90, which displays the recirculation efficiency.

It should be appreciated that the present invention will function in substantially the same way if the locations of the exciting coil 72 and sensing coil 74 are reversed.

Referring now to FIGS. 1 and 2, to use the recirculation monitor 22 to perform a recirculation test the dialysis system operator injects a bolus of a marker fluid into the treated blood in the dialyzer outlet line 32 at the needle access site 50 using a typical hypodermic needle 92. The marker fluid may have an electrical conductivity that is higher or lower than the fluid flowing in the outlet line 32. In the preferred embodiment a high conductivity marker fluid is used to avoid damaging blood cells. In the preferred embodiment the bolus is 1 milliliter of 24 percent hypertonic saline solution. The conductivity of the treated blood being returned to the patient through the dialyzer outlet line 32 and the outlet conductivity cell 52 of the recirculation monitor 22 is altered. This altered conductivity blood enters the fistula through the outlet needle 34.

If the flow balance in the fistula 26 is such that no flow is recirculating the altered conductivity blood will exit the fistula, as illustrated by the flow circulation arrow 94, without altering the conductivity of the blood within the fistula. If, however, the flow balance within the fistula 26 is such that blood is recirculating, as illustrated by flow circulation arrow 96, a portion of the blood withdrawn from the fistula 26 by the pump 36 will be the altered conductivity blood. The recirculation monitor 22 measures the conductivity of the blood flowing in the outlet line 32 and the conductivity of the blood flowing in the inlet line 30 and quantitatively determines the difference between those conductivities continuously throughout the recirculation test. The sensing logic and display circuit 90 interprets the quantitative conductivity differences measured by the recirculation monitor 22 to determine recirculation efficiency.

Figure 4:
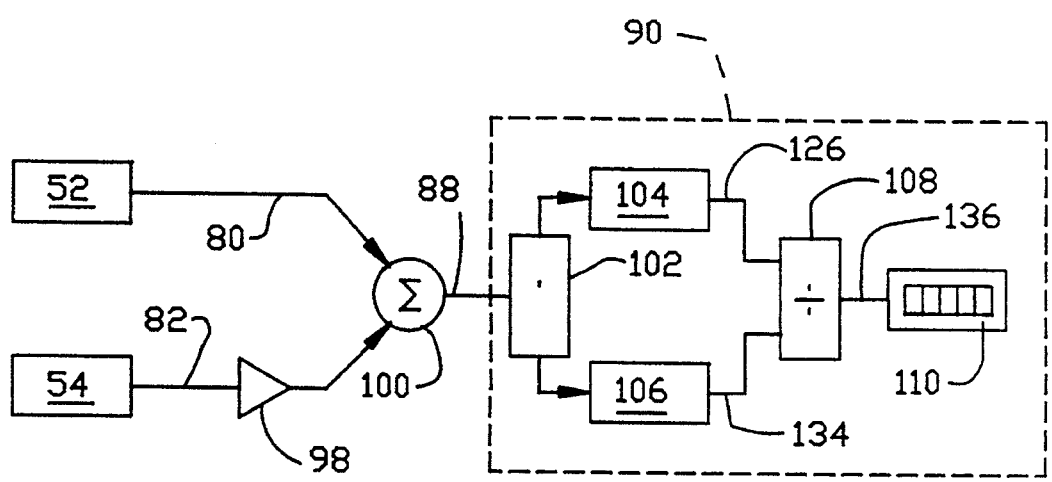
FIG. 4 is an electrical block diagram of sensing logic usable with the differential conductivity recirculation monitor illustrated in FIGS. 2 and 3.

The determination of recirculation efficiency will be explained by reference to FIGS. 4, 5 and 6. The outlet conductivity cell 52 and the inlet conductivity cell 54 may be thought of as signal generators generating the induced currents 80 and 82 in the outlet and inlet conductivity cells. The induced current 82 of the inlet conductivity cell 54 is inverted 98 and added 100 to the induced current 80 in the outlet conductivity cell 52, by virtue of the physical relationships between the conductivity cells, excitation coil 72 and sensing coil 74, to produce the sensed current 88.

The sensing logic and display circuit 90 performs a zeroing operation 102, a dialyzer outlet flow determining operation 104, and unrecirculated flow determining operation 106, and a dividing operation 108, and includes a visual display device 110, preferably a liquid crystal display. Alternatively the functions of the sensing logic and display circuit 90 may be performed by a digital computer (not shown).

Figure 5:
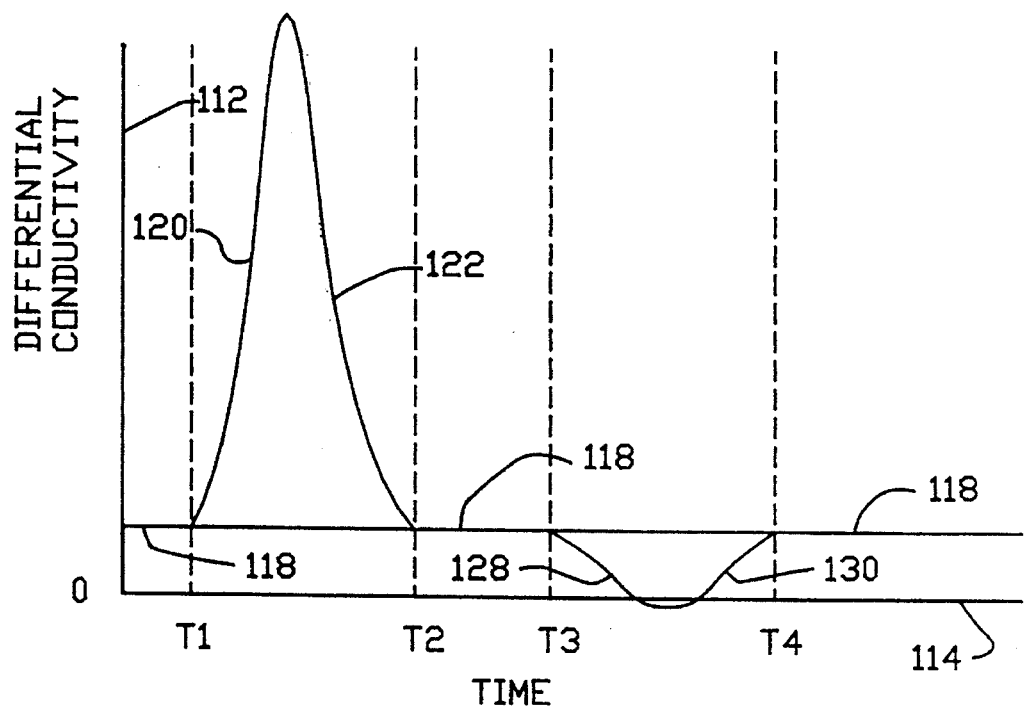
FIG. 5 is a graph illustrating differential conductivity versus time during a recirculation test employing the differential conductivity recirculation monitor shown in FIG. 2.
Figure 6:
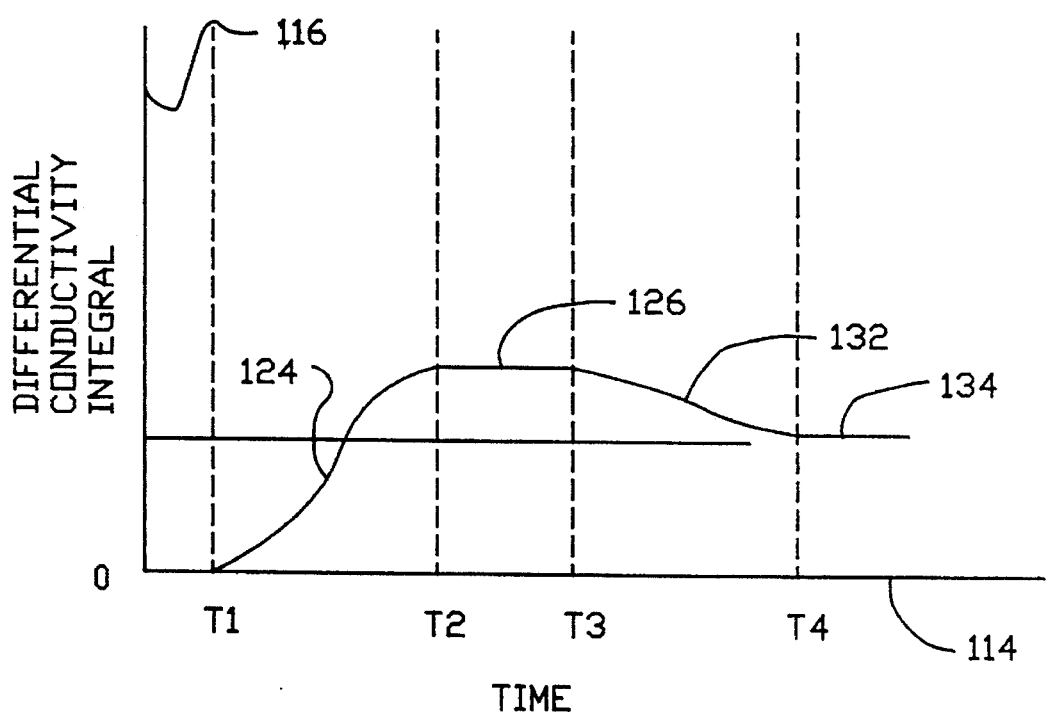
FIG. 6 is a graph illustrating the integral of differential conductivity versus time during a recirculation test employing the differential conductivity recirculation monitor shown in FIG. 2, having substantially the same time scale as FIG. 5.

FIG. 5 is a graph illustrating differential conductivity (reference 112) as a function of time (reference 114) during a typical recirculation test. FIG. 6 is a graph illustrating the integral of differential conductivity (reference 116) as a function of time 114 during the typical recirculation test. Prior to the beginning of the recirculation test there may be some normal difference (reference 118) between the conductivity of the treated blood in the dialyzer outlet line 32 (FIG. 2) and the untreated blood in the dialyzer inlet line 30 (FIG. 2). This normal conductivity difference 118 is subtracted from the sensed current 88 by the zeroing operation 102 of the sensing logic and display circuit 90 to remove the effect of the normal difference in conductivity 118 from determination of recirculation efficiency. The recirculation test begins (reference time T1) when the bolus of high conductivity fluid is injected into the dialyzer outlet line 32 (FIG. 2) at the needle access site 50 (FIG. 2). The conductivity of the treated blood in the dialyzer outlet line 32 (FIG. 2) is increased. As the bolus passes through the outlet conductivity cell 52 (FIG. 2) the differential conductivity 112 increases (reference 120) and then decreases (reference 122) until the normal conductivity difference 118 is reached (reference time T2). The outlet flow determining operation 104 calculates the integral of conductivity from the start of the test (reference time T1) until the differential conductivity returns to the normal value 118 (reference time T2). The integral 116 of the conductivity increases (reference 124) until a first steady state value (reference 126) of the integral 116 is reached when the differential conductivity 112 returns to the normal value 118 (reference time T2). The first steady state value 126 is stored by the outlet flow determining operation 104 and is representative of the flow of treated blood in the dialyzer outlet line 32 (FIG. 2).

After the treated blood with the altered conductivity enters the fistula 26 (FIG. 1) a portion of it may recirculate and be withdrawn from the fistula 26 (FIG. 1) through the dialyzer inlet line 30 (FIG. 2). The conductivity of the untreated blood in the inlet conductivity cell 54 is increased (reference time T3), causing the differential conductivity to decrease 128 and then increase 130, returning to the normal value of conductivity difference 118 (reference time T4). The integral of differential conductivity from the beginning of the recirculation test (reference time T1) until the normal value of conductivity difference 118 is reached again (reference time T4) is calculated by the unrecirculated flow determining operation 106 of the sensing logic and display circuit 90. The integral of differential conductivity 116 decreases (reference) to a second steady state value 134 (reference time T4.

The second steady state value 134 of the integral of differential conductivity is stored by the unrecirculated flow determining operation 106 of the sensing logic and display circuit 90 and is representative of the portion of the bolus of high conductivity liquid that was not recirculated. The second steady state value 134 is thus representative of the unrecirculated portion of the treated blood flow. The dividing operation divides the second steady state value 134 by the first steady state value 126 to calculate a recirculation efficiency 136. The recirculation efficiency 136 is provided to the operator as a visual output by the display device 110.

It will be apparent to those skilled in the art that the sensing logic and display circuit 90 may be implemented using analog or digital circuit devices and that other calculation algorithms may be used to calculate recirculation efficiency 138. Further, the recirculation efficiency 138 may be calculated in real time or, alternatively, the necessary data stored and the calculations performed on the stored data.

Further details of the preferred embodiment of the differential conductivity recirculation monitor will be explained by reference to FIGS. 7–11.

Figure 7:
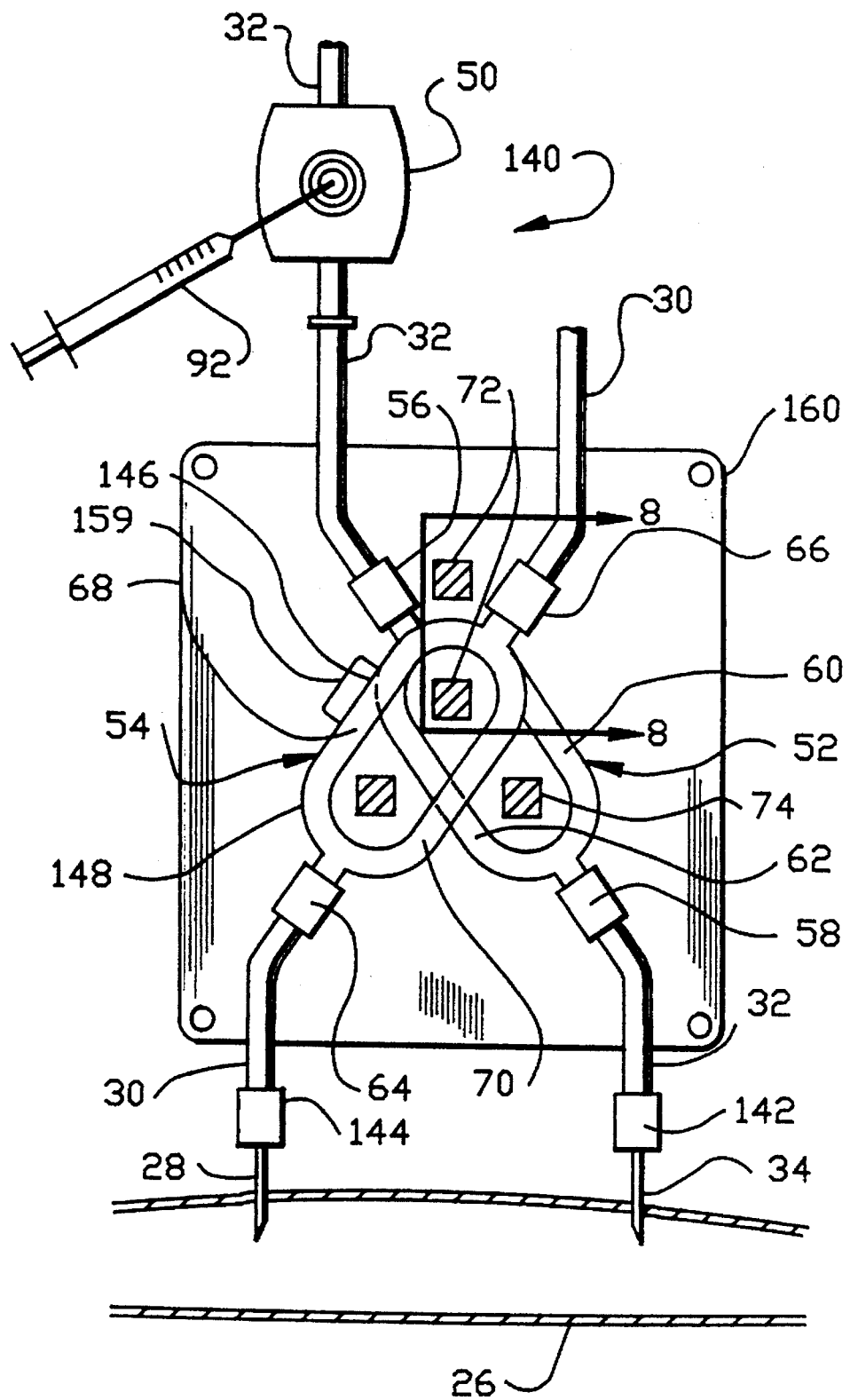
FIG. 7 is a partial elevational view of a tubing set and sectional view of an excitation and sensing unit for use with the dialysis system shown in FIG. 1, incorporating the differential conductivity recirculation monitor in accordance with the present invention.

FIG. 7 illustrates a portion of a typical disposable tubing set 140 incorporating conductivity cells 52 and 54 in accordance with the present invention. As is well known in the art, it is highly desirable for all portions of the tubing set 140 to be used with a dialysis system to be disposable, in order to prevent cross contamination and infection between patients. This is true of most blood and other biological or medical fluid processing systems.

Disposable tubing sets may be formed from a plurality of plastic tubes, connectors, needles and medical devices using techniques that are well known in the art. The discussion of the tubing set 140 will therefore be limited to a discussion of the differential conductivity recirculation monitor 22 (FIG. 1) portion of the tubing set.

The dialyzer outlet line 32 is a plastic tube which extends through the needle access site 50, into the outlet conductivity cell 52. The outlet conductivity cell 52 comprises a plastic conduit loop and includes the upstream connection 56, elongated divided first and second tubing branches 60 and 62, and the downstream connector 58. The downstream connector 58 has mounted in it an extension of the dialyzer outlet line 32, which is mounted through a connector 142 to the outlet needle 34.

The dialyzer inlet needle 28 is connected through a connector 144, to the dialyzer inlet line 30. The dialyzer inlet line 30 is connected to the inlet conductivity cell 54, which includes the upstream connection 64, elongated divided third and fourth tubing branches 68 and 70 respectively, and downstream connector 66. The dialyzer inlet line 30 extends from the downstream connector 66 to the dialyzer apparatus 24 (FIG. 1).

In the preferred embodiment the portion of the dialyzer outlet line 32 between the dialyzer outlet needle 34 and the downstream connector 58 of the outlet conductivity cell 52 and the portion of the dialyzer inlet line 30 between the dialyzer inlet needle 28 and the upstream connector 64 of the inlet conductivity cell 54 must be sufficiently long so that the bolus of marker fluid passes completely through the outlet conductivity cell before any altered conductivity fluid from the fistula 26 enters the inlet conductivity cell.

Figure 8:
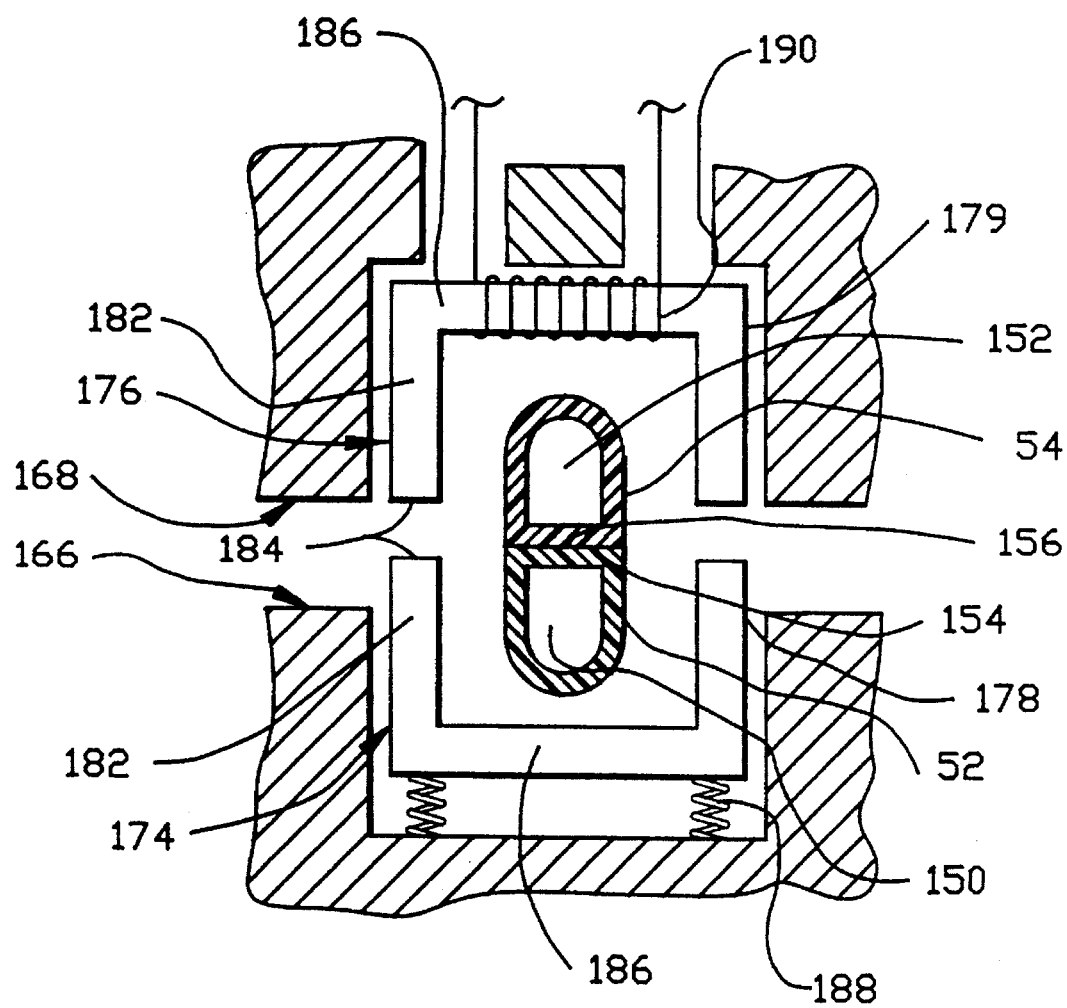
FIG. 8 is a partially diagrammatic sectional view taken substantially at line 8—8 in FIG. 7.

The conductivity cells 52 and 54 have the overall shape of links in an ordinary chain, straight side portions 146 being joined at their ends by semicircular portions 148. In cross-section at the excitation location, as shown in FIG. 8, the wall of each conductivity cell 42 and 54 defines a D, the insides of the Ds providing conduit portions 150 and 152. A flat portion 154 of the D of the outlet conductivity cell 52 is abutted and adhered to a flat portion 156 of the D of the inlet conductivity cell 54 along one pair of semicircular portions 148 of the conductivity cells. The other pair of circular portions 148 are separated so that axes of the conductivity cells 52 and 54 define therebetween an angle of approximately sixty degrees. The flat portions 154 and 156 of the conductivity cells 52 and 54 are further joined along two of the straight portions 146 at a location along the second and fourth tubing branches 62 and 70, respectively at the sensing location. An orientation tab 159 is formed on the inlet conductivity cell 54.

Figure 9:
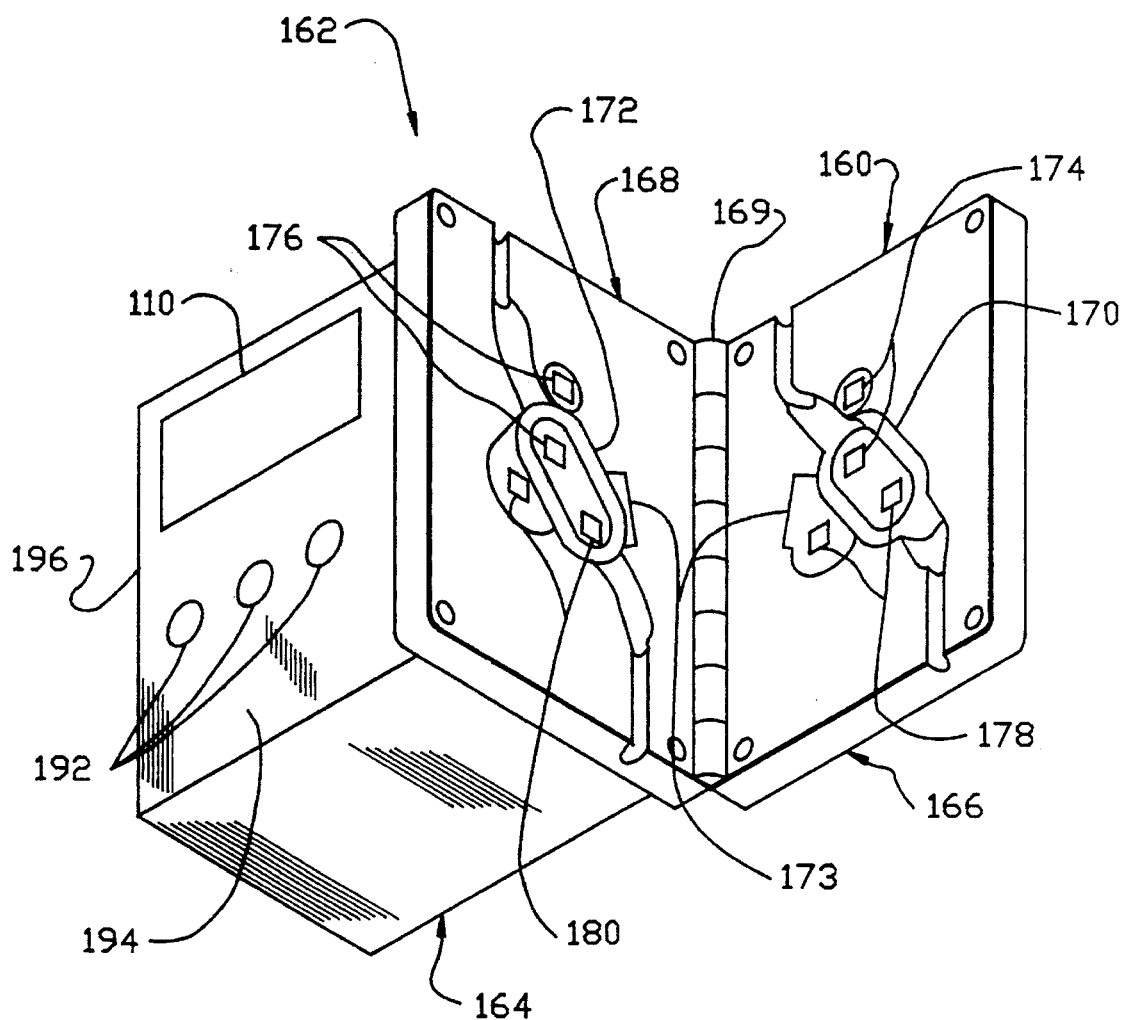
FIG. 9 is a partially diagrammatic perspective view of the excitation and sensing unit of the differential conductivity recirculation monitor of the present invention.

Mating with tube set 140 is a tubing set acceptor 160. As shown in FIG. 9, the tubing set acceptor 160 comprises a portion of an excitation and sensing unit 162 which also includes a logic circuit module 164. The tubing set acceptor 160 comprises a portion of a first, or rear, acceptor plate 166 and a second, or front, acceptor plate 168 joined by a hinge 169 for motion between open and closed positions and provided with a latch or spring (not shown) to hold the acceptor plates in the closed position. The first acceptor 166 plate is relieved to accept into appropriately-shaped indentations 170 thereof the outlet conductivity cell 52 (FIG. 2) and portions the tubing set 140 (FIG. 7). The second acceptor plate 168 is relieved to accept into appropriately-shaped indentations 172 thereof the inlet conductivity cell 54 and portions of the tubing set 140 (FIG. 7). An orientation tab recess 173 is defined by at least one of the appropriately shaped indentations 170 and 172. The orientation tab recess 173 cooperates with the orientation tab 159 (FIG. 7) of the tubing set 140 (FIG. 7) to assure that the tubing set is correctly oriented when installed in the tubing set acceptor 160.

The tubing set acceptor 160 is sufficiently large to support the conductivity cells 52 and 54 and enough of the dialyzer outlet line 32 and dialyzer inlet line 30 so that fluid flow patterns through the conductivity cells are substantially repeatable, being relatively unaffected by bends, curves, tubing movement, and other disturbances or variations in the positions of the outlet and inlet lines with respect to the conductivity cells during measurement.

The excitation coil 72 and sensing coil 74 are mounted to the tubing set acceptor 160. The excitation coil 72 and sensing coil, 74 are positioned at right angles to each other to minimize magnetic interference between the coils. The excitation coil 72 comprises a first, or rear, and a second, or front, half core 174 and 176, respectively. Similarly the sensing coil comprises a third, or rear, and a fourth, or front, half-core 178 and 180 respectively. The first and third half-cores 174 and 178, respectively are mounted to the first acceptor plate 166 and the second and third half cores 176 and 180 respectively are mounted to the second acceptor plate 186.

As illustrated in FIG. 8, each half core has a U-shaped configuration, with short legs 182 having ends 184 and connecting legs 186. The tubing set acceptor 160 holds a portion of the tubing set 140 which includes the conductivity cells 52 and 54 in a fixed relationship with the excitation coil 72 and sensing coil 74.

The first and second half cores 174 and 176 are oriented so that their ends 184 abut when the first and second acceptor plates 166 and 168 are brought to the closed position. The excitation coil 72 thus formed is in the shape of a rectangle defining a rectangular window. The third and fourth half cores 178 and 180 are similarly oriented so that their ends abut when the first and second acceptor plates 166 and 168 are brought to the closed position. The sensing coil 74 thus formed is also in the shape of a rectangular ring defining a rectangular window (not shown). When a tubing set 140 is placed in the tubing set acceptor 160 the first and third tubing branches 60 and 68 are engaged in the window of the excitation coil 72 and the second and fourth tubing branches 62 and 70 are engaged in the window of the sensing coil 74 so that the coils encircle the corresponding tubing branches. Biasing springs 188 may be provided to hold corresponding half-cores in firm contact when the acceptor plates 166 and 168 are closed.

The legs 182 and 186 of the coil 72 and 74 are square in cross-section. At least one connecting leg 186 of each coil 72 and 74 is transformer wire wrapped 190.

The logic circuit module 164 of the excitation and sensing unit 162 may be mounted to one of the acceptor plates 168 or may be separate from the tubing set acceptor 160 with wiring interconnections (not shown) to the tubing set acceptor 160. The logic circuit module houses the sensing logic and display circuit 90, with the display device 110 and one or more manual input switches 192 to enable the operator to perform such functions as turning the recirculation monitor on and off, testing the operation of the monitor and initiating recirculation test.

Although the display device 110 and manual input switches 192 are shown in FIG. 9 as being on a side 194 of the logic circuit module 164 adjacent to the second acceptor plate 168, in the preferred embodiment the display device and manual input switches may be on a side 196 opposite the second acceptor plate 168, or any other side of the logic circuit module.

The circuitry for conductivity measurement and calibration may suitably be as set forth in the Ogawa patent incorporated by reference above.

The preferred embodiment of the present invention has been described by reference to determination of recirculation efficiency in a surgically created blood access site during, or in conjunction with, a hemodialysis procedure. It should be understood that the present invention is not so limited. The present invention may be used in a variety of medical and non-medical circumstances where it is desirable to determine recirculation efficiency. Further, it should be understood that the present invention may be used in a variety of medical and non-medical circumstances where it is desirable to compare the electrical conductivities of two fluids. Presently preferred embodiments of the present invention and many of its aspects, features and advantages have been described with a degree of particularity. It should be understood that this description has been made by way of preferred example, and that the invention is defined by the scope of the following claims.

What is claimed is:

1. A method for quantitatively determining a degree of recirculation flow within a zone of a vessel into which a first fluid having a first electrical conductivity is being inserted and from which a second fluid having a second electrical conductivity is simultaneously being withdrawn, comprising:

altering the electrical conductivity of the first fluid;

measuring the electrical conductivity of the first fluid after the conductivity is altered and before the first fluid is inserted into the zone of the vessel;

measuring the electrical conductivity of the second fluid after it is withdrawn from the zone of the vessel; and comparing the conductivity of the first fluid with the conductivity of the second fluid to quantitatively determine the degree of recirculation flow in the zone of the vessel.

2. A method as defined in claim 1 wherein:

the step of altering the electrical conductivity of the first fluid further comprises:

injecting a marker fluid having an electrical conductivity different from the conductivity of the first fluid into the first fluid.

3. A method as defined in claim 1 wherein the steps of measuring the conductivity of the first fluid and the second fluid further comprise:

flowing the first fluid through a first conduit, said first conduit comprising a first conductivity cell with a continuous path configuration;

flowing the second fluid through a second conduit, said second conduit comprising a second conductivity cell with a continuous path configuration;

inducing a first electrical current in the first fluid in the first conductivity cell and a second electrical current in the second fluid in the second conductivity cell;

sensing the first electrical current in the first fluid in the first conductivity cell and the second electrical current in the second fluid in the second conductivity cell; and subtracting the second electrical current from the first electrical current to produce a signal representative of the difference in the conductivities between the first and the second fluids.

4. A method as defined in claim 3 wherein the inducing step further comprises:

positioning an exciting electromagnetic coil in proximity with the first and second conductivity cells at an inducing location;

inducing the first electrical current in an electrical direction along the continuous path of the first conductivity cell; and simultaneously inducing the second electrical current to flow in the same electrical direction along the continuous path of the second conductivity cell as the direction of the first electrical current.

5. A method as defined in claim 4 further comprising:

alternating the electrical direction of each of the electrical currents in the first and second conductivity cells.

6. A method as defined in claim 5 wherein the sensing and subtracting steps further comprise:

positioning a sensing electromagnetic coil in proximity with the first and second conductivity cells at a sensing location with the first conductivity cell oriented at the sensing location with the first electrical current in an opposite electrical direction with respect to the sensing electromagnetic coil from the electrical direction of the second electrical current with respect to the sensing electromagnetic coil.

7. A method as defined in claim 6 wherein:

the exciting electromagnetic coil defines a window through which the first and the second conductivity cells pass; and the sensing electromagnetic coil defines a window through which the first and the second conductivity cells pass.

8. A method as defined in claim 4 wherein the sensing and subtracting steps further comprise:

positioning a sensing electromagnetic coil in proximity with the first and second conductivity cells at a sensing location, the first conductivity cell being oriented at the sensing location with the first electrical current in an opposite electrical direction with respect to the sensing electromagnetic coil from the electrical direction of the second electrical current with respect to the sensing electromagnetic coil.

9. A method as defined in claim 3 wherein:

the zone of the vessel is a surgically formed arteriovenous fistula;

the first conduit is an outlet line of a medical device for blood processing;

the second conduit is an inlet line of the medical device for blood processing;

the first fluid is blood processed by the medical device for blood processing; and the second fluid is blood to be processed by the medical device for blood processing.

10. A method as defined in claim 9 wherein the medical device for blood processing is a hemodialysis device.

11. A method as defined in claim 9 wherein the step of altering the conductivity of the first fluid further comprises:

injecting hypertonic saline solution into the blood processed by the medical device for blood processing at a point in the outlet line before the blood passes through the first conductivity cell.

12. A method as defined in claim 3 further comprising:

determining a value representative of a normal difference between the electrical conductivity of the first fluid and the electrical conductivity of the second fluid before the step of altering the electrical conductivity of the first fluid is performed; and subtracting the value representative of the normal differences between the conductivity of the first fluid and the conductivity of the second fluid from the signal representative of the difference in the conductivities between the first and the second fluids.

13. A method as defined in claim 12 further comprising:

integrating the difference in conductivity from the beginning of a recirculation test until an altered conductivity portion of the first fluid has completely passed through the first conductivity cell to produce a first steady state value;

integrating the difference in conductivity from the beginning of a recirculation test until a portion of the second fluid with conductivity altered by recirculation of the first fluid in the vessel has completely passed through the second conductivity cell to produce a second steady state value; and dividing the second steady state value by the first steady state value to produce a value of recirculation efficiency.

14. A method as defined in claim 13 further comprising:

visually displaying the value of recirculation efficiency.

15. An apparatus for quantitatively determining a degree of recirculation flow within a zone of a vessel into which a first fluid having a first electrical conductivity is being inserted and from which a second fluid having a second electrical conductivity is simultaneously being withdrawn, comprising:

means for altering the electrical conductivity of the first fluid; and means for measuring the electrical conductivity of the first fluid after the conductivity is altered and before the first fluid is inserted into the zone of the vessel, for measuring the electrical conductivity of the second fluid after it is withdrawn from the zone of the vessel, and for comparing the conductivity of the first fluid with the conductivity of the second fluid to quantitatively determine the degree of recirculation flow in the zone of the vessel.

16. An apparatus as defined in claim 15 wherein:

the means for altering the electrical conductivity of the first fluid further comprises:
   means for injecting a marker fluid having an electrical conductivity different than the conductivity of the first fluid into the first fluid.

17. An apparatus as defined in claim 13 wherein the means for measuring the conductivity of the first fluid and the second fluid and comparing the conductivities further comprises:

a first conduit through which the first fluid flows to the zone of the vessel, said first conduit comprising a first conductivity cell with a first conductivity cell upstream connection, a first conductivity cell downstream connection, and two branches connecting the upstream connection to the downstream connection with a continuous path configuration from the upstream connection to the downstream connection through one of the two branches and returning to the upstream connection through the other one of the two branches;

a second conduit through which the second fluid flows from the zone of the vessel, said second conduit comprising a second conductivity cell with a second conductivity cell upstream connection, a second conductivity cell downstream connection, and two branches connecting the upstream connection to the downstream connection with a continuous path configuration from the upstream connection to the downstream connection through one of the two branches and returning to the upstream connection through the other one of the two branches;

means for inducing a first electrical current in the first fluid in the first conductivity cell and a second electrical current in the second fluid in the second conductivity cell;

means for sensing the first electrical current in the first fluid in the first conductivity cell and the second electrical current in the second fluid flowing in the second conductivity cell, and subtracting the second electrical current from the first electrical current to produce a signal representative of the difference in the conductivities between the first and the second fluids.

18. An apparatus as defined in claim 17 wherein:

the inducing means comprises an exciting electromagnetic coil in proximity with the first and second conductivity cells at an exciting location, the first conductivity cell being oriented at the exciting location with respect to the second conductivity cell with first electrical current in an electrical direction with respect to the exciting electromagnetic coil and the second electrical current in the same electrical direction with respect to the exciting electromagnetic coil.

19. An apparatus as defined in claim 18 wherein:

the electrical direction of the first and second electrical currents in the first and the second conductivity cells alternates.

20. An apparatus as defined in claim 19 wherein:

the sensing and subtracting means further comprises:

a sensing electromagnetic coil in proximity with the first and second conductivity cells at a sensing location, the first conductivity cell being oriented at the sensing location with respect to the second conductivity cell with the electrical direction of the first electrical current with respect to the sensing electromagnetic coil opposite the electrical direction of the second electrical current with respect to the sensing electromagnetic coil.

21. An apparatus as defined in claim 20 wherein:

the exciting electromagnetic coil defines a window through which one branch of each of the first and the second conductivity cells pass; and the sensing electromagnetic coil defines a window through which the other branch of each of the first and the second conductivity cells pass.

22. An apparatus as defined in claim 21 wherein:

each one of the sensing and the exciting electromagnetic coils comprises a front and a rear half core, separable to insert the branch of each of the first and second conductivity cells into the window of the coil and to remove the branch of each of first and second conductivity cells from the window of the coil.

23. An apparatus as defined in claim 22 further comprising:

a front acceptor plate having a rear side to which the front sensing coil half core and the front exciting coil half core are mounted, each half core being mounted so that the window is formed to the rear of the front half core;

a rear acceptor plate having a front side to which the rear sensing coil half core and the rear inducing coil half core are mounted, each half core being mounted so that the window is formed to the front of the rear half core; and joining means for joining the front acceptor plate to the rear acceptor plate in a parallel relationship with the front half core of the exciting coil mated with the rear half core of the exciting coil and the front half core of the sensing coil mated with the rear half coil of the sensing coil.

24. An apparatus as defined in claim 23 wherein the joining means further comprises:

a hinge joining the front acceptor plate to the rear acceptor plate; and a latch to hold the front acceptor plate in the parallel relationship with the rear acceptor plate.

25. An apparatus as defined in claim 18 wherein the sensing and subtracting means further comprises:

a sensing electromagnetic coil in proximity with the first and second conductivity cells at a sensing location, the first conductivity cell being oriented with respect to the second conductivity cell at the sensing location with the electrical direction of the first electrical current with respect to the sensing electromagnetic coil opposite the electrical direction of the second electrical current with respect to the sensing electromagnetic coil.

26. An apparatus as defined in claim 17 wherein:

the zone of the vessel is a surgically formed fistula;

the first conduit is an outlet line of a medical device for blood processing;

the second conduit is an inlet line of the medical device for blood processing;

the first fluid is blood processed by the medical device for blood treatment; and the second fluid is blood to be processed by the medical device for blood processing.

27. An apparatus as defined in claim 26 wherein the medical device for blood processing is a hemodialysis device.

28. An apparatus as defined in claim 26 wherein the means for altering the conductivity of the first fluid further comprises:

a hypodermic needle access site at a point in the outlet line before the blood passes through the first conductivity cell.

29. An apparatus for determining a degree of recirculation flow of blood in a surgically formed fistula in a patient, the fistula being connected to a blood processing device by an inlet conduit for withdrawing blood from the fistula and delivering the blood to the blood processing device and an outlet conduit for returning blood to the fistula from the blood processing device, comprising:

an outlet conductivity cell formed in the outlet conduit, the outlet conductivity cell having an upstream connection in fluid communication with the blood processing device, a downstream connection in fluid communication with the fistula and two branches connecting the upstream connection to the downstream connection with a continuous path configuration from the upstream connection to the downstream connection through one of the two branches and returning to the upstream connection through the other one of the two branches;

an inlet conductivity cell formed in the inlet conduit, the arterial conductivity cell having an upstream connection in fluid communication with the fistula, a downstream connection in fluid communication with the blood processing device and two branches connecting the upstream connection to the downstream connection with a continuous path configuration from the upstream connection to the downstream connection through one of the two branches and returning to the upstream connection through the other one of the two branches;

a hypodermic needle access site in the inlet conduit located between the upstream connection of the inlet conductivity cell and the blood processing means;

an exciting electromagnetic coil encircling one of the branches of the outlet conductivity cell at an exciting location and one of the branches of the inlet conductivity cell at the exciting location to induce a first electrical current in blood in the outlet conductivity cell in an electrical direction with respect to the exciting coil and to induce a second electrical current in blood in the inlet conductivity cell in the same electrical direction with respect to the exciting coil as the first electrical current;

a sensing electromagnetic coil encircling the other one of the branches of the outlet conductivity cell at a sensing location and the other one of the branches of the inlet conductivity cell at the sensing location, the other branches being oriented with the first electrical current and the second electrical current in opposite electrical directions with respect to the sensing coil; and means electrically connected to the sensing electromagnetic coil for producing a signal representative of the difference between the magnitude of the first electrical current and the magnitude of the second electrical current.

30. An apparatus as defined in claim 29 wherein:

the electrical direction of each of the first and second electrical currents alternates with respect to the exciting coil.

31. An apparatus as defined in claim 29 wherein:

the exciting electromagnetic coil defines a window through which one branch of each of the outlet and inlet conductivity cells pass;

the sensing electromagnetic coil defines a window through which the other branch of each of the outlet and inlet conductivity cells pass; and each one of the sensing and the exciting electromagnetic coils comprises a front and a rear half core, separable to insert the corresponding branch of each of the outlet and inlet conductivity cells into the window of the coil and to remove the corresponding branch of each of the conductivity cells from the window of the coil.

32. An apparatus as defined in claim 31 further comprising:

a front acceptor plate having a rear side to which the sensing coil front half core and the exciting coil front half core are mounted, each half core being mounted so that the window is formed to the rear of the front half core;

a rear acceptor plate having a front side to which the sensing coil rear half core and the exciting coil rear half core are mounted, each half core being mounted so that the window is formed to the front of the rear half core; and joining means for joining the front half plate to the rear half plate in a parallel relationship with the front half core of the exciting coil mated with the rear half core of the exciting coil and the front half core of the sensing coil mated with the rear half core of the sensing coil.

33. An apparatus as defined in claim 29 wherein the blood processing device is a hemodialysis device.

34. A method for quantitatively determining a degree of recirculation flow of fluids having a physical property within a zone of a vessel into which a first fluid having a first initial value of the physical property is being inserted and from which a second fluid having a second initial value of the physical property is simultaneously being withdrawn, comprising:

altering the value of the physical property of the first fluid;

measuring the value of the physical property of the first fluid after the value of the physical property is altered and before the first fluid is inserted into the zone of the vessel;

measuring the value of the physical property of the second fluid after it is withdrawn from the zone of the vessel; and comparing the measured altered value of the physical property of the first fluid with the measured value of the physical property of the second fluid to quantitatively determine the degree of recirculation flow in the zone of the vessel.

35. A method as defined in claim 34 wherein:

the step of altering the value of the physical property of the first fluid further comprises:

injecting a marker fluid having a value of the physical property different from the value of the physical property of the first fluid.

36. An apparatus for determining a degree of recirculation flow of fluids having a physical property within a zone of a vessel into which a first fluid having a first initial value of the physical property is being inserted and from which a second fluid having a value of the physical property is simultaneously being withdrawn, comprising:

means for altering the value of the physical property of the first fluid;

means for measuring the value of the physical property of the first fluid after the value of the property is altered and before the first fluid is inserted into the zone of the vessel;

means for measuring the value of the physical property of the second fluid after it is withdrawn from the zone of the vessel; and means for comparing the measured altered value of the physical property of the first fluid with the measured value of the physical property of the second fluid to quantitatively determine the degree of recirculation flow in the zone of the vessel.

37. An apparatus as defined in claim 36 wherein:

the means for altering the value of the physical property of the first fluid further comprises:

means for injecting a marker fluid having a value of the physical property different than the first initial value of the physical property.

38. An apparatus as defined in claim 15 further comprising:

a tubing set wherein the means for measuring the electrical conductivity of the first fluid after the conductivity is altered and before it is inserted into the zone of the vessel, for measuring the electrical conductivity of the second fluid after it is withdrawn from the zone of the vessel, and for comparing the conductivity of the first fluid with the conductivity of the second fluid comprises:

a first conduit adapted to convey the flow of the first fluid after its conductivity is altered and before it is inserted into the zone of the vessel and within which the conductivity of the first fluid is measured, said first conduit comprising a first conductivity cell with a first conductivity cell upstream connection, a first conductivity cell downstream connection, and two branches connecting the upstream connection to the downstream connection with a continuous path configuration from the upstream connection to the downstream connection through one of the two branches and returning to the upstream connection through the other one of the two branches; and a second conduit adapted to convey the flow of the second fluid after it is withdrawn from the zone of the vessel and within which the conductivity of the second fluid is measured, said second conduit comprising a second conductivity cell with a second conductivity cell upstream connection, a second conductivity cell downstream connection, and two branches connecting the upstream connection to the downstream connection with a continuous path configuration from the upstream connection to the downstream connection through one of the two branches and returning to the upstream connection through the other one of the two branches.

39. An apparatus as defined in claim 38 wherein the first conductivity cell is adjacent to the second conductivity cell at a first junction in a generally parallel relationship.

40. An apparatus as defined in claim 39 wherein the first conductivity cell is adjacent to the second conductivity cell at a second junction in a generally angular relationship.

41. An apparatus as defined in claim 40 wherein:

each of the first and the second conductivity cells comprise tubing with cross-sectional configuration defined by a generally semicircular sidewall and an adjacent flat sidewall;

the flat sidewall of the first conductivity cell adjoins the flat sidewall of the second conductivity cell at the first junction; and the flat sidewall of the first conductivity cell adjoins the flat sidewall of the second conductivity cell at the second junction.

42. An apparatus as defined in claim 38 wherein:

the zone of the vessel is a surgically formed arteriovenous fistula;

the first conduit is an outlet line of a medical device for blood processing; and the second conduit is an inlet line of the medical device for blood processing.

43. An apparatus as defined in claim 42 wherein the medical device for blood processing is a hemodialysis device.

44. An apparatus as defined in claim 38 wherein:

the means for altering the electrical conductivity of the first fluid comprises:

a hypodermic needle access site in the first conduit of the tubing set in fluid communication with the first conductivity cell upstream connection.

* * * * *